United States Patent [19]

Kashkai

[11] 4,353,789
[45] Oct. 12, 1982

[54] GAS-LIQUID ANALYZER

[76] Inventor: Chingiz M. O. Kashkai, ulitsa Azizbekova, 8, kv. 6, Baku, U.S.S.R.

[21] Appl. No.: 276,591

[22] Filed: Jun. 23, 1981

[30] Foreign Application Priority Data

Feb. 5, 1981 [SU] U.S.S.R. ............................ 2965818

[51] Int. Cl.³ ..................... G01N 27/28; G01N 27/30
[52] U.S. Cl. ............................................. 204/195 R
[58] Field of Search .......... 204/195 R, 195 B, 195 F, 204/195 G, 195 M; 422/81, 82; 364/497

[56] References Cited

U.S. PATENT DOCUMENTS

| | | | |
|---|---|---|---|
| 2,870,078 | 1/1959 | Hood | 204/195 R |
| 2,930,967 | 3/1960 | Laird et al. | 204/195 R X |
| 3,151,052 | 9/1964 | Arthur et al. | 204/195 F |
| 3,327,204 | 6/1967 | Hillier et al. | 204/195 R X |
| 3,997,420 | 12/1976 | Buzza | 204/195 P |

FOREIGN PATENT DOCUMENTS 2000297 1/1979 United Kingdom ............ 204/195 R

OTHER PUBLICATIONS

H. F. Osswald et al., Chimia, 31, No. 2, Feb. 1977.

Primary Examiner—G. L. Kaplan
Attorney, Agent, or Firm—Ladas & Parry

[57] ABSTRACT

A gas-liquid analyzer comprises a sample conveying assembly having a capillary tube with a sample under analysis, the walls of the tube being provided with two rows of openings arranged in opposition to each other. The openings of one of the rows accommodate hermetically secured ion-selective electrodes connected to a switching unit wired with a potentiometer and a potential corrector. Secured in the openings of another row are porous inserts adapted to contact electrolyte. The presence of sample under analysis between the porous insert and the ion-selective electrode causes the latter to come into contact with a reference electrode electrically connected to the potentiometer.

9 Claims, 5 Drawing Figures

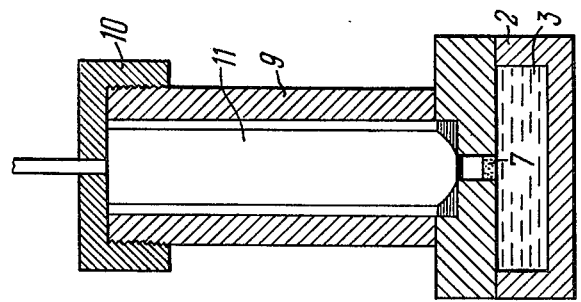
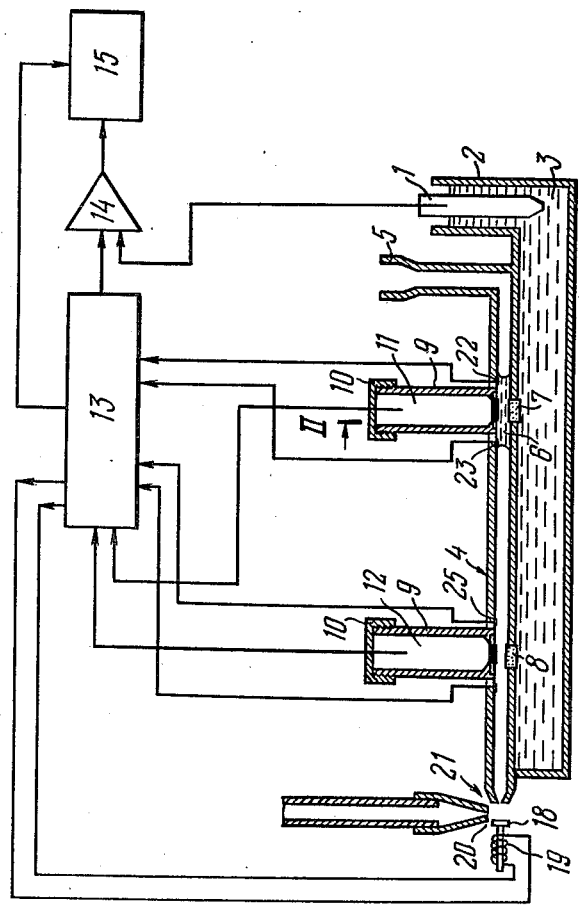

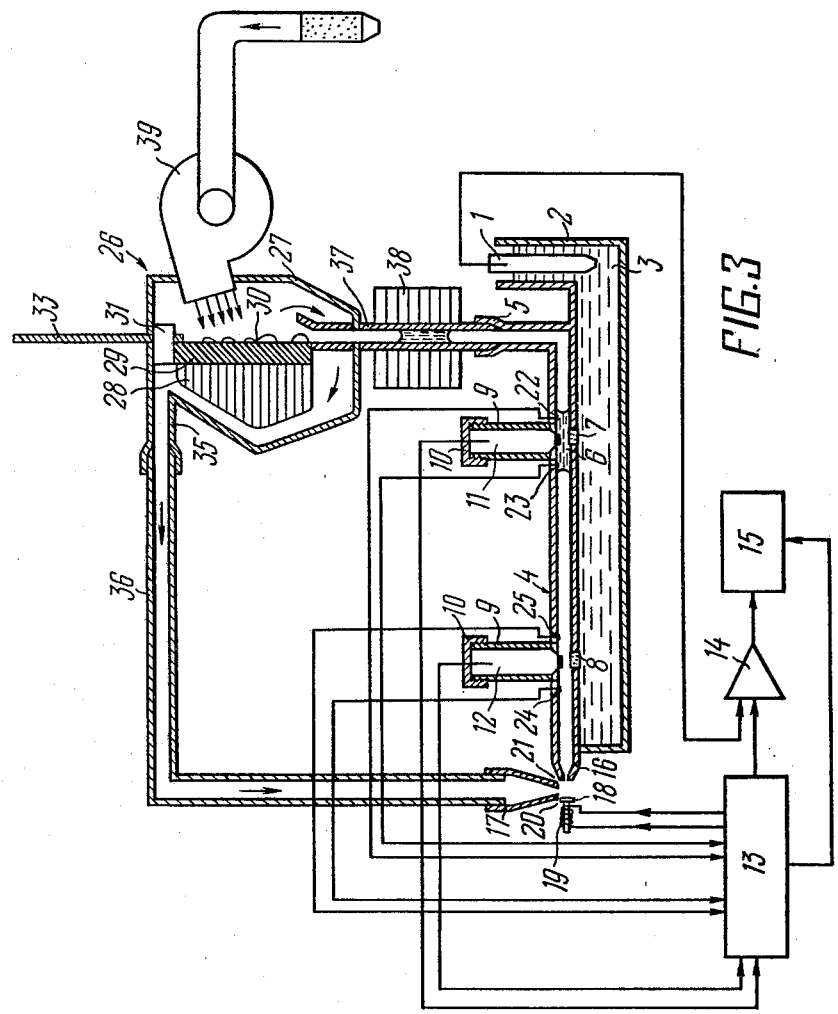

GAS-LIQUID ANALYZER

FIELD OF THE INVENTION

The present invention relates to the techniques used for electrochemical analysis, and more particularly to gas-liquid analyzers.

The invention can find application in ecological examinations for determination of the amount of pollution in the atmosphere and natural waters, for conducting biochemical analysis and for continuous systematic observations over the changing parameters of the samples being analyzed.

The invention can be employed most advantageously for gas- and hydrogeochemical explorations of mineral deposits.

Also, the invention can be used for determining the composition of air or liquid media.

BACKGROUND OF THE INVENTION

Modern advances in the rate of industrial production call for higher quality and efficiency of sample analysis, and consequently for improved gas-liquid analyzers. This is especially the case with gas-liquid analyzers used in the field conditions.

There is known a gas-liquid analyzer (cf., e.g., "Perenosny ionomer—Portable Ionometer," Gomel, the Polespechat Publishers, 1973, pp. 10 and 36) comprising a reference electrode immersed in electrolyte, ion-selective electrodes alternately contacting the reference electrode, an assembly for conveying a sample under analysis to the ion-selective electrodes for the latter to alternately contact with the sample under analysis, a potentiometer electrically connected with the reference electrode and one of the ion-selective electrodes, and a potential corrector electrically wired with the potentiometer. In the above analyzer the sample conveying assembly for conveying the sample under analysis to the ion-selective electrodes has the form of a vessel with two openings, one of the openings receiving the reference electrode, while another opening is used for introducing the sample to be analyzed and also accommodates one of the ion-selective electrodes.

However, the analyzer suffers from a disadvantage because the ion-selective electrodes must be alternately introduced into the vessel filled with the sample under analysis only during the analysis, while each of the electrodes must be connected to the potentiometer, which negatively affects the efficiency of the analysis.

Also, another disadvantage of the above analyzer resides in that during analyzing small volumes of samples a certain portion thereof is withdrawn from the vessel together with the electrode being retracted, as a result of which the minimal useful volume of the sample under analysis depends on the number of analytical measurements.

Further, the manual means of conveying the sample to the ion-selective electrodes, as well as their manual replacement and switching operations complicate servicing the analyzer.

SUMMARY OF THE INVENTION

It is an object of the invention to provide a gas-analyzer of higher efficiency.

Another object is to simplify sample analysis.

This is attained by that in a gas-liquid analyzer comprising a reference electrode immersed in electrolyte, ion-selective electrodes adapted to alternately contact the reference electrode, a sample conveying assembly for conveying a sample under analysis to alternately come into contact with the ion-selective electrodes, a potentiometer electrically connected with the reference electrode and one of the ion-selective electrodes, and a potential corrector electrically connected with the potentiometer, according to the invention, the sample conveying assembly incorporates a capillary tube the wall of which accommodates disposed in opposition to each other two rows of openings with the number of such openings essentially equal to the number of the ion-selective electrodes hermetically secured in the openings of one of the rows, porous inserts secured in the openings of another of the rows for contact with the sample under analysis and with the electrolyte, and a sample displacement means communicating with the capillary tube, whereas the analyzer per se additionally comprises a switching unit electrically connected with the ion-selective electrodes, the sample displacement means and the potentiometer.

Preferably, the sample displacement means comprises located in proximity to an outlet end of the capillary tube a nozzle for creating an air jet and an electrically actuated gate connected to the switching unit.

Preferably, the analyzer comprises a water vapours condenser having a chamber accommodating a thermoelement provided with a cooling surface and a liquid outlet communicating with an inlet end of the capillary tube, a heat-exchanger for equalizing the temperature of the sample under analysis with the temperature of the surrounding medium secured on the liquid outlet of the chamber, and an air pump communicating with the chamber.

Preferably, the water vapours condenser additionally comprises a slidable heat-insulating shield the edge of which contacts upon movement the cooling surface of the thermoelement.

Preferably, the analyzer additionally comprises a means for monitoring the presence of a sample under analysis adapted to contact with the sample during the passage thereof between the porous insert and the corresponding ion-selective electrode and electrically connected to the switching unit.

Advantageously, use is made of contact pairs equal in number to the number of the ion-selective electrodes to serve as the means for monitoring the presence of a sample under analysis, the contacts of each of the pairs being adapted to penetrate inside the capillary tube in locations close to the ion-selective electrodes and to electrically close in the presence of the sample under analysis.

It is also preferable in some instances that the capillary tube be fabricated from a transparent material.

The present invention enables to carry out analyses of any number of components of the sample under analysis in a continuous mode of analytical measurements, thereby improving the efficiency of the analytical operations.

The invention also affords to convey without losses a sample to be analyzed to practically any number of ion-selective electrodes, which makes it possible to employ a minimum volume of sample required for conducting analyses.

Further, the invention permits to condense the air vapors for determination of the composition thereof which extends the range of application of the analyzer of the invention.

In addition, the invention allows to automate the process of sampling and successive analysis of all sample components, which simplifies servicing the analyzer according to the invention, especially in the field conditions.

BRIEF DESCRIPTION OF THE DRAWINGS

Other objects and advantages of the present invention will become more fully apparent during consideration of the exemplary embodiments thereof in conjunction with the accompanying drawings, in which:

FIG. 1 shows a sectional elevation of a gas-liquid analyzer according to the invention;

FIG. 2 is a section taken along the line II—II in FIG. 1;

FIG. 3 is a general sectional elevation of another modification of the gas-liquid analyzer according to the invention provided with a water vapors condenser;

DETAILED DESCRIPTION OF THE INVENTION

Figure 4:
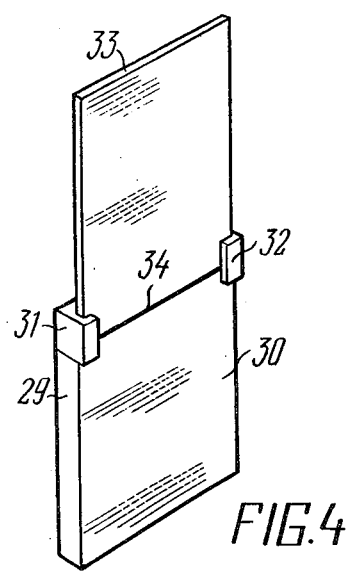
FIG. 4 shows a perspective view of a thermoelement with a heat-insulating shield.

Disclosed by way of example hereinbelow will be a gas-liquid analyzer intended for exploration of mineral deposits.

With reference to FIG. 1, a gas-liquid analyser comprises a reference electrode 1 immersed in a bath 2 filled with electrolyte 3. Adapted to directly overlie the bath 2 is a capillary tube 4, inlet end 5 of which receives a sample 6 under analysis. The wall of the capillary tube 4 is provided with two rows of openings disposed in opposition to each other, each row comprising two such openings. The openings of one row accommodate porous inserts 7 and 8 in intimate contact with both the electrolyte 3 and the sample 6 during the passage of the latter inside the tube 4. Arranged to overlie the openings of another row are hermetically secured sleeves 9 covered by pressure caps 10. Inside the sleeves 9 and over the openings of the tube 4 there are positioned ion-selective electrodes 11 and 12 intended to alternately come into contact with the sample 6 during the passage thereof inside the tube 4 and at the same time contact the electrolyte 3 by way of the inserts 7 and 8. The capillary tube 4 (FIGS. 1 and 2) is generally a small volume tube of rectangular cross-section. The analyzer further comprises electrically series connected switching unit 13 (FIG. 1), potentiometer 14 and potential corrector 15, the unit 13 being also directly wired to the potential corrector 15. The electrodes 11 and 12 are connected to the switching unit 13. The electrode 1 electrically communicates with the potentiometer 14. Outlet end 16 of the capillary tube 4 accommodates nozzle 17 to supply a jet of air and electrically actuated gate 18 connected with the switching unit 13 via an electromagnet 19. The nozzle 17 and gate 18 with the electromagnet 19 represents a means for displacing the sample under analysis, this means being generally designated by 20, while the means 20 in conjunction with the capillary tube 4 make up assembly 21 for conveying a sample to be analyzed. Arranged in close proximity to each of the electrodes 11 and 12 to pass inside the capillary tube 4 are pairs of electrical contacts 22, 23 and 24, 25, respectively. The pair of contacts 22 and 23 are adapted to close or interconnect when the sample 6 is caused to pass therethrough; the same applies to the pair of contacts 24 and 25. These pairs of contacts 22, 23 and 24, 25 are intended as a means indicating the presence of a sample under analysis.

According to another modified form as represented in FIG. 3, the gas-liquid analyzer comprises a water vapour condenser 26 having a chamber 27; located inside the chamber 27 and secured to a radiator 28 is a thermoelement 29 having a cooling surface 30. Affixed to the thermoelement 29 are guides 31 and 32 (FIGS. 3 and 4) accommodating slidably a heat-insulating shield 33 insertable through an aperture provided in the chamber 27 in such a manner, that edge 34 of the shield is adapted to contact the cooling surface 30 of the thermoelement 29. An air outlet 35 (FIG. 3) communicates with the nozzle 17 via a pipe 36. Connected with the inlet end 5 of the capillary tube 4 is a liquid condensate outlet 37 provided with a heat-exchanger 38 for equalizing the temperature of the sample to be analyzed with the temperature of the surrounding medium. Secured in a window in the wall of the chamber 27 facing the cooling surface 30 of the thermoelement 29 is an outlet of an air pump 39.

Figure 5:
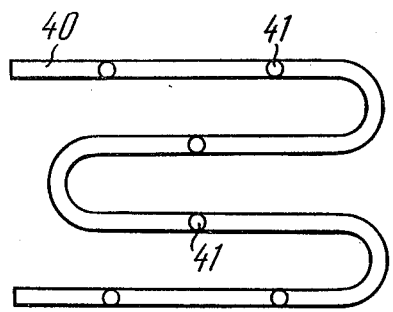
FIG. 5 shows a modification of a capillary tube according to the invention provided with six openings in one row.

According to yet another modification, a serpentine-shaped capillary tube 40 (FIG. 5) has six openings 41 in one row.

As is known, some mineral deposits can be detected by geochemical prospecting of waters and gases. This calls for numerous compositional analyses of natural waters and gases to be conducted in field conditions to determine areas featuring abnormal occurrence of ore or trace element to thereby make a judgement on further exploration of undiscovered ore fields.

The gas-liquid analyzer works in two operating modes.

In the case of the hydrogeochemical explorations, that is when it is required to determine the composition of natural waters, the analyzer operates as follows.

The sample 6 to be analyzed is supplied to the inlet end 5 (FIG. 1) of the capillary tube 4 of the assembly 21. The means 20 for displacing the sample under analysis is then actuated, wherefor the outlet end 16 of the capillary tube 4 is blown off by a jet of air escaping from the nozzle 17. With the gate 18 in an open position, an underpressure is produced in the capillary tube 4 causing displacement of the sample 6. Upon reaching the ion-selective electrode 11, the sample 6 closes the contacts 22 and 23 used for monitoring the presence of sample under analysis, thereby completing the circuit between the electrode 11 and the reference electrode 1 through the porous insert 7. Closure of the contacts 22 and 23 acts to engage the switching unit 13 of any conventional construction. The switching unit 13 causes the gate 18 to shut the outlet end 16 of the capillary tube 4, whereby the sample 6 is held between the electrode 11 and insert 7; therewith, the unit 13 also communicates the electrode 11 with the potentiometer 14. At the same time, the switching unit 13 transmits to the potential corrector 15 information on the serial number of the electrode 11 in operation. The corrector 15 acts to correct the readings of the potentiometer 14 depending on the type and parameters of the operating ion-selective electrodes (viz. the electrode 11). After the analytical measurements of a first component of the sample 6 under analysis have been completed, the switching unit 13 breaks the circuit of the electrode 11 and opens the gate 18 to thereby cause the sample 6 to move further along the capillary tube 4 towards the subsequent electrode 12. The operating cycle is then recommenced with the electrode 12 in operation, whereafter following the completion of the measurements of a second components the sample 6 is discharged through the outlet end 16 of the capillary tube 4.

The samples under analysis may be conveyed through the capillary tube 4 either intermittently or continuously. In the latter case, the underpressure produced by the sample displacement means 20 may automatically draw the sample 6 into the tube 4 provided the inlet end 5 thereof is in permanent contact with a liquid to be sampled.

In the second operating mode, that is for geochemical explorations of gaseous substances or when it is required to conduct compositional analysis of air, the gas-liquid analyzer according to the invention operates in the following manner.

The air pump 39 (FIG. 3) acts to force the air under analysis through the opening in the chamber 27 of the condenser 26 against the cooling surface 30 of the thermoelement 29. At the temperature of the thermoelement 29 below the dew point, water vapors are condensed on the cooling surface 30 thereof to drip into the liquid outlet 37 of the chamber 27. The thus formed solution is essentially the sample 6 containing the air constituents dissolved therein. Under the action of the underpressure produced by the sample displacement means 20, the sample 6 is then conveyed through the heat-exchanger 38 to equalize its temperature with the temperature of the surrounding atmosphere and thereafter reach the inlet end 5 of the capillary tube 4. The analytical process that follows is generally similar to the one described with reference to the aforedescribed first operating mode.

If the air to be sampled features low humidity and high temperature, the required quantity of the sample 6 may be produced by means of the heat-insulating shield 33. For this purpose, prior to air sampling, the surface 30 of the thermoelement must be covered by the shield 33, which substantially lowers the temperature of the surface 30. Thereafter, the shield 33 is slided upwards along the guides 31 and 32; the air to be sampled is then supplied, after which the shield 33 is moved downwards along the surface 30. The edge 34 of the shield 33 removes the condensed solution from the surface 30 to drip into the liquid outlet 37 of the chamber 27.

In view of the aforegoing, the use of the heat-insulating shield 33 facilitates condensing the water vapors and affords to reduce the volume of air being sampled for analysis.

In the course of condensing, the cooled and dried air passes through the radiator 28 and is further conveyed via the air outlet 35 of the chamber 27 along the pipe 36 to the nozzle 17, wherefrom it escapes to produce an underpressure in the capillary tube 4.

By virtue of the rectangular cross-section of the capillary tube 4, a minimum volume of the sample 6 under analysis can be used for a maximum contact area with the electrodes, such as with the electrode 12.

For the cases when it is sufficient to provide visual monitoring of the location of the sample 6 in the capillary tube 4 or 40 (FIGS. 1, 2, 3 and 5), the tube is preferably fabricated from a transparent material.

For taking analytical measurements of a larger number of components of the sample 6 under analysis the capillary tube 40 (FIG. 5) of serpentine shape is preferable to employ a larger number of the ion-selective electrodes without increasing the overall size of the analyzer.

The analyzer according to the invention is simple to operate.

Also, the analyzer according to the invention affords to conduct sampling and analysis continuously.

The present invention further enables to reduce the overall size of the analytical apparatus.

What is claimed is:

1. A gas-liquid analyzer comprising:
   a bath;
   electrolyte filling up said bath;
   a reference electrode immersed in said electrolyte;
   a potentiometer having first and second inputs and outputs, the first input thereof being connected to said reference electrode;
   a switching unit having a first group of inputs, a second group of inputs, first, second, third and fourth outputs, said first output thereof being connected to said second input of said potentiometer;
   a potential corrector having first and second inputs, said first and second inputs thereof being connected with said output of said potentiometer and said second output of said switching unit, respectively;
   a sample conveying assembly;
   a capillary tube of said sample conveying assembly having a wall, an inlet end, and an outlet end, the capillary tube being arranged to overlie said bath; the capillary tube further comprising first and second rows of openings arranged in opposition in said wall;
   a group of porous inserts of said sample conveying assembly located in said openings of said first row of openings and adapted to intimately contact said electrolyte;
   a sample displacement means of said sample conveying assembly, the sample displacement means being disposed in close proximity to said outlet end of said capillary tube and connected with said third and fourth outputs of said switching unit;
   a group of ion-selective electrodes equal in number to the number of said porous inserts and hermetically secured in said openings of said second row of openings, each of the electrodes being connected to one of said inputs of said first group of inputs of said switching unit;
   said sample under analysis which is introduced into said inlet end of said capillary tube adapted during displacement thereof to alternately contact with one of said ion-selective electrodes and one of said porous inserts positioned to face such ion-selective electrode.

2. An analyzer as claimed in claim 1, wherein said sample displacement means comprises:
   a nozzle for the supply of air positioned close to said outlet end of said capillary tube;
   a gate arranged in front of said outlet end of said capillary tube to underlie said nozzle.

3. An analyzer as claimed in claim 1 comprising:
   a condenser of water vapours;
   a chamber of said condenser of water vapours having a wall and air and liquid outlets, the chamber being connected by the liquid outlet thereof with said inlet end of said capillary tube; a hole being provided in said wall;
   a thermoelement of said water vapours condenser having a cooling surface and disposed inside said chamber so that said cooling surface faces said hole in said wall of said chamber;

a heat-exchanger for equalizing the temperature of said sample under analysis with the temperature of the surrounding medium, the heat-exchanger being secured on said liquid outlet of said chamber;

an air pump having an outlet, the outlet being secured in said hole of said chamber.

4. An analyzer as claimed in claim 3 comprising:

a means of monitoring the presence of a sample under analysis adapted to come into contact with said sample under analysis during the passage of said sample between said porous insert and said corresponding ion-selective electrode and electrically connected to said group of inputs of said switching unit.

5. An analyzer as claimed in claim 4 wherein used as said means of monitoring the presence of a sample under analysis are pairs of contacts equal in number to the number of said ion-selective electrodes, said contacts of each of said pairs being adapted to penetrate inside said capillary tube in locations close to each said ion-selective electrode, said contacts being electrically connected to said inputs of said second group of inputs of said switching unit and adapted to close in the presence of said sample under analysis.

6. An analyzer as claimed in claim 3 wherein said capillary tube is fabricated from a transparent material.

7. An analyzer as claimed in claim 1 comprising:

a means of monitoring the presence of a sample under analysis adapted to come into contact with said sample under analysis during the passage of said sample between said porous insert and said corresponding ion-selective electrode and electrically connected to said second group of inputs of said switching unit.

8. An analyzer as claimed in claim 7 wherein used as said means of monitoring the presence of a sample under analysis are pairs of contacts equal in number to the number of said ion-selective electrodes, said contacts of each of said pairs being adapted to penetrate inside said capillary tube in locations close to each said ion-selective electrode, said contacts being electrically connected to said inputs of said second group of inputs of said switching unit and adapted to close in the presence of said sample under analysis.

9. An analyzer as claimed in claim 1 wherein said capillary tube is fabricated from a transparent material.

* * * * *